United States Patent [19]
Köckerling et al.

[11] Patent Number: 5,474,570
[45] Date of Patent: Dec. 12, 1995

[54] SURGICAL SUTURE CLAMP, IN PARTICULAR PURSE STRING SUTURE CLAMP

[76] Inventors: Ferdinand Köckerling, Hindenburgstrasse 28a, D-91o54 Erlangen; Ignaz Schneider, Hauptstrasse 52, D-91301 Forchheim, both of Germany

[21] Appl. No.: 201,649

[22] Filed: Feb. 25, 1994

[30] Foreign Application Priority Data

Mar. 17, 1993 [DE] Germany .......................... 43 08 454.0

[51] Int. Cl.⁶ .................................................. A61B 17/04
[52] U.S. Cl. ............................................ 606/174; 606/207
[58] Field of Search ........................... 606/174, 205–209, 606/210

[56] References Cited

U.S. PATENT DOCUMENTS

| | | | |
|---|---|---|---|
| 4,643,190 | 2/1987 | Heimberger | 606/205 |
| 4,994,079 | 2/1991 | Genese . | |
| 5,152,778 | 10/1992 | Bales, Jr. et al. | 606/174 X |
| 5,188,636 | 2/1993 | Fedotov . | |
| 5,254,125 | 10/1993 | Porter et al. | 606/170 X |
| 5,308,358 | 5/1994 | Bond et al. | 606/174 X |
| 5,314,440 | 5/1994 | Shapiro | 606/174 |
| 5,338,317 | 8/1994 | Hasson et al. | 606/206 |

FOREIGN PATENT DOCUMENTS

| | | |
|---|---|---|
| 0119967 | 9/1984 | European Pat. Off. . |
| 0512725 | 11/1992 | European Pat. Off. . |
| 3126121 | 4/1984 | France . |
| 9203041 | 6/1992 | France . |
| 9213263 | 3/1993 | France . |
| 4127812A1 | 2/1993 | Germany . |
| 2081099 | 2/1982 | United Kingdom . |

Primary Examiner—Peter A. Aschenbrenner
Assistant Examiner—Nancy Mulcare
Attorney, Agent, or Firm—Laff, Whitesel, Conte & Saret, Ltd.

[57] ABSTRACT

A surgical suture clamp is provided with two clamp jaws positioned movably one in relation to the other in a forceps-like manner. It is formed as an endoscopable suture clamp to be inserted into the body through a trocar and provided with a leading tube, in the vicinity of the inner tube end of which, to be lead into the body, at least one clamp jaw is positioned to be pivotably driven in relation to the second clamp jaw. A drive is arranged in the portion of the outer tube end remaining outside the body and is coupled by way of a transmission with the at least one pivotably driven clamp jaw.

11 Claims, 2 Drawing Sheets

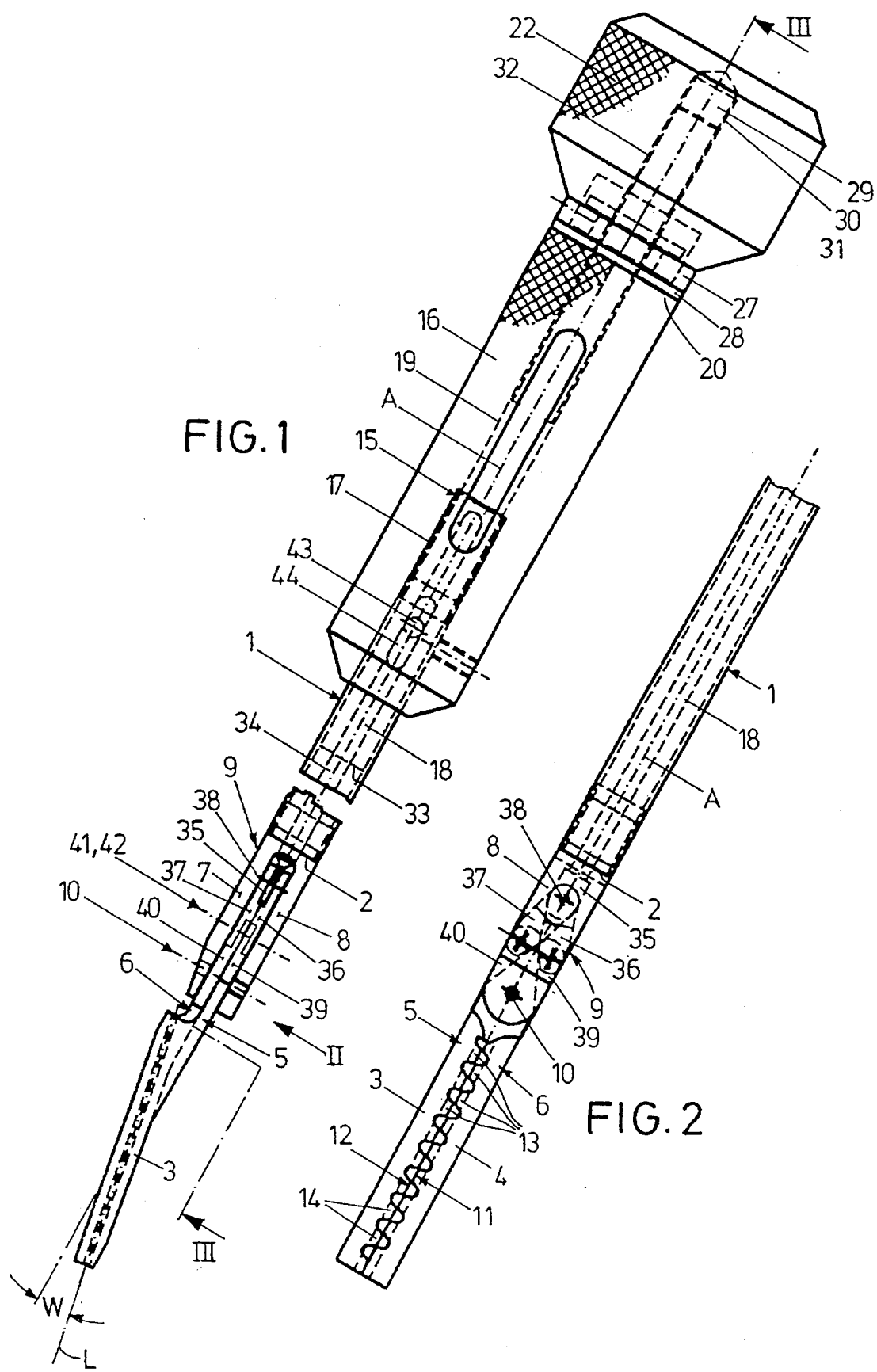

5,474,570

SURGICAL SUTURE CLAMP, IN PARTICULAR PURSE STRING SUTURE CLAMP

BACKGROUND OF THE INVENTION

1. Field of the Invention

The invention relates to a surgical suture clamp, in particular a purse string suture clamp for applying a purse string suture during the performance of gastric, intestinal and pulmonary operations or the like, with two clamping jaws movably positioned one in relation to the other in a forceps-like manner.

2. Background Art

A conventional, comparatively long surgical cut into the abdominal wall has so far been necessary to apply a purse string suture with the aid of the suture clamp mentioned at the outset for instance for closing the colon during the performance of certain intestinal operations such as partial intestinal removal. Because of the scissors-like configuration of the suture clamp there has so far been no possibility to apply such a suture in so-called endoscopic surgery where the necessary observation instruments such as endoscopes and surgical instruments are inserted via trocars which pierce the abdominal wall. In this regard certain operations requiring for instance a purse string suture to be applied are not feasible with the means of endoscopic surgery.

SUMMARY OF THE INVENTION

Proceeding from these problems it is accordingly the object of the invention to specify a surgical suture clamp and in particular a purse string suture clamp of the generic kind which is suitable for the purposes of endoscopic surgery.

This object is attained by the features wherein the suture clamp is structured as an endoscopable suture clamp, to be lead into the body via a trocar, with a leading-in tube, in the vicinity of an inner tube end of which, to be lead into the body, at least one clamp jaw is positioned to be pivotably driven in relation to the second clamp jaw, and wherein a drive means is arranged in the vicinity of an outer tube end remaining ouside the body and is coupled, by way of a transmission, with the at least one pivotably driven clamp jaw for the opening and the closing of the suture clamp. Accordingly, the suture clamp is structured as an endoscopable suture clamp, to be lead into the body via a trocar, with a leading-in tube, in the vicinity of the inner tube end of which, to be lead into the body, at least one clamp jaw is positioned to be pivotably driven in relation to the second clamp jaw. Further, a drive is arranged in the vicinity of the outer tube end remaining ouside the body and is coupled, by way of a transmission, with the at least one pivotably driven clamp jaw.

By reason of this configuration it is possible to use the suture clamp for the purposes of endoscopic surgery, it being understood that the tube as well as in particular the clamp jaws provided at the inner tube end are arranged and dimensioned, at least in their closed position, such that these parts fit through the inside opening of the trocar, the latter thus serving as a sluice provided in the abdominal wall for the suture clamp.

In keeping with a preferred embodiment the clamp jaws of the endoscopic suture clamp are arranged in their longitudinal direction at a small acute angle to the longitudinal axis of the leading-in tube. This inclination helps to achieve that a needle passage formed in the clamp jaws is readily accessible from both ends of the clamp jaws. On the other hand, the clamp jaws, when closed, remain within the contours of the leading-in tube referred to the latter's longitudinal axis, so that the suture clamp can be pushed through the inside opening of the trocar even with its clamp jaws inclined.

Further features, details and advantages of the invention will become apparent from the sub-claims and the ensuing description of an example of embodiment of the subject matter of the invention taken in conjunction with the attached figures.

BRIEF DESCRIPTION OF THE DRAWINGS

FIG. 1 is a lateral view of a purse string suture clamp according to the invention, FIG. 2 is a lateral view of the clamp seen from the direction of the arrow II of FIG. 1 with the clamp jaws closed.

DESCRIPTION OF THE PREFERRED EMBODIMENT

Figure 3:
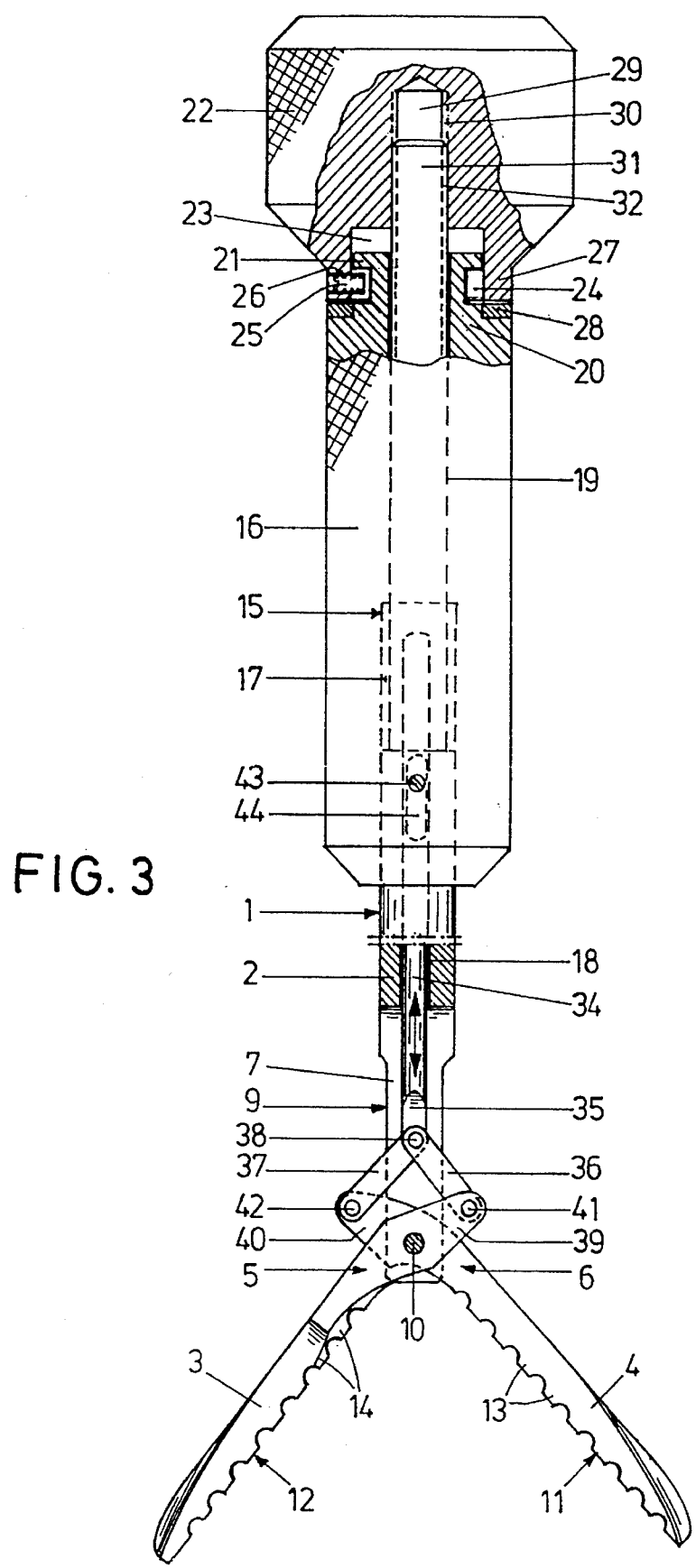
FIG. 3 is a lateral view, partially cut along the section line III—III of FIG. 1, of the clamp from the direction of the arrow II with the clamp jaws opened.

An endoscopic purse string suture clamp according to the invention, as illustrated in FIGS. 1 to 3, has a leading-in tube 1 as its main component, which is pilotable into the body via a trocar (not shown) in the abdominal wall of the patient. In the vicinity of the inner tube end insertable into the body, two clamp jaws 3, 4 are positioned to be pivotably driven, each clamp jaw 3, 4 being formed as an arm of a double-armed clamp lever 7, 8. The latter are positioned between the fork legs 7, 8 of a forked bearing head 9 secured to the inner tube end 2 to be pivotable by means of a common pivot axis 10.

The clamp faces 11, 12, facing each other, of the clamp jaws 3, 4 are structured undulatorily as usual, the elevations 13 on the clamp faces 11, 12 being passed through by a needle passage 14 extending in the longitudinal direction L of the clamp jaws 3, 4 and shown in dashed lines in FIGS. 1 and 2. In the closed position of the clamp, a thread is passed through these needle passages 14 unidirectionally with the aid of needles for applying a purse string suture.

In their closed position (FIGS. 1, 2) the two clamp jaws 3, 4 extend in their longitudinal direction L at a small acute angle W to the longitudinal axis A of the leading-in tube. This angle W is approximately 10° and is dimensioned such that the clamp jaws 3, 4 in their closed position (FIG. 1, 2) are within the circular contour of the leading-in tube referred to a direction of view of the clamp jaws 3, 4 extending in parallel to the longitudinal axis A of the tube 1. As a result of this inclination the orifices of the needle passage 14 are comfortably accessible, which is of special advantage when needles are entered into the needle passage 14 with the aid of an endoscopic manipulator.

A substantially cylindrical handle member 16 is coaxially screwed on to the external tube end 15, remaining outside the body, of the leading-in tube 1 by means of a screw connection 17, the handle member 16 having a continuous inner bore 19 extending coaxially with the tube orifice 18. An annular shoulder 21 likewise extending coaxially, on which a spindle wheel 22 is arranged rotatably with its cylindrical internal opening 23, is provided at the front end 20, facing away from the leading-in tube 1, of the handle member 16. A circumferential groove 24, with which headless screws 25 engage as projections, is further provided on the circumference of the annular shoulder 21. These headless screws are screwed through corresponding threaded bores 26 in the annular collar 27 around the cylindrical internal opening 23 of the spindle wheel 22 and arrest the latter in the longitudinal axial direction of the leading-in tube 1. A sliding ring 28 from brass is inserted between the front side of the annular collar 27 and the handle member 16.

With its blind-hole bore 29 which, proceeding from the internal opening 23, is arranged coaxially to the longitudinal axis A of the leading-in tube 1 and has an internal thread 30, the spindle wheel 22 forms, together with a threaded bolt 31 in the inner bore 19 of the handle member 16, a spindle drive for the clamp jaws 3, 4. To this end the external thread 32 of the threaded bolt 31 is in engagement with the internal thread 30 in the spindle wheel 22. At its end 33 facing away from the spindle wheel 22 the threaded bolt 31 is further connected with a push bar 34 leading to the forked bearing head 9 where it ends within the two fork legs 7, 8. Two articulated lever bars 36, 37 are articulated with their ends on this corresponding end 35 of the push bar 34 by means of a common articulated axle 38. The two other ends of the articulated lever bars 36, 37 are connected with the two operating arms 39, 40 of the clamp levers 5, 6 for articulation by way of articulated axles 41, 42. By reason of the above described construction the threaded bolt 31 together with the push bar 34 and the two articulated lever bars 36, 37 form a transmission for transmitting the rotary actuation originating from the spindle wheel 22 to the two clamp levers 5, 6. In this case, the unit of the threaded bolt 31 and the push bar 34 is further arrested in the direction of rotation. For the purpose of this arrest of rotation the threaded bolt 31 is provided on its outside with a radially projecting elevation in the form of a screw head 43 of a screw radially screwed into the threaded bolt, which screw head 43 engages with an oblong hole 44 extending parallel to the longitudinal axis A of the leading-in tube 1 in the latter.

The opening and closing of the clamp jaws 3, 4 is made as follows:

Starting from the closed position, shown in FIGS. 1 and 2, of the two clamp jaws 3, 4, in which the articulated lever bars 36, 37 and the operating arms 39, 40 lie within the two fork legs 7, 8 of the forked bearing head 9, the spindle wheel 22 is actuated to rotate. Due to the arrest of rotation of the threaded bolt 31 and the push rod 34, the rotary movement of the spindle wheel 22 is translated in the way of a spindle drive into a pushing movement of the threaded bolt 31 and the push rod 34 in the direction towards the inner tube end 2 of the leading-in tube 1. As a result of this pushing and of the approach of the articulated axle 38 towards the pivot axis 10 of the two clamp levers 5, 6, the two articulated lever bars 36, 37 move apart outwards and consequently, spread open the two operating arms 39, 40 of the clamp levers 5, 6 (FIG. 3). The clamp jaws 3, 4 are thus moved into their opened position.

For closing the clamp jaws 3, 4 the spindle wheel 22 is actuated in the opposite direction of rotation, whereby the threaded bolt 31 is displaced with the push bar 34 in the opposite direction coaxially to the longitudinal axis A, thus causing the two clamp levers 5, 6 to be retracted by way of the articulated lever bars 36, 37.

What is claimed is:

1. A surgical suture clamp, in particular a purse string suture clamp for applying a purse string suture during the performance of gastric, intestinal and pulmonary operations, comprising two clamp jaws (3, 4) movably positioned one in relation to the other in a forceps-like manner, wherein the suture clamp is structured as an endoscopable suture clamp, to be lead into the body via a trocar, with a leading-in tube (1), in the vicinity of an inner tube end (2) of which, to be lead into the body, at least one clamp jaw (3) is positioned to be pivotably driven in relation to the second clamp jaw (4), wherein a drive means (22) is arranged in the vicinity of an outer tube end (15) remaining outside the body and is coupled, by way of a transmission (31, 34), with the at least one pivotably driven clamp jaw (3, 4) for the opening and the closing of the suture clamp, wherein in a closed position the clamp jaws (3, 4) in their longitudinal direction (L) extend at a small acute angle (W) to the longitudinal axis (A) of the leading-in tube (1), and wherein the clamp jaws (3,4) each comprise a needle passage (14) extending in the longitudinal direction (L) of the clamp jaws (3,4).

2. A suture clamp according to claim 1, wherein the drive and the transmission are formed as a spindle drive with a spindle wheel (22) arrested longitudinally axially in relation to a tube axis (A) and positioned coaxially rotatably thereto and a push bar (34) arrested in the direction of rotation and longitudinally axially displaceable in the leading-in tube (1), which push bar (34), with an external thread (32) at its outer end, is in engagement with an internal thread (30) of the spindle wheel (22) and which, with its inner end (35), is coupled for articulation with the at least one pivotably positioned clamp jaw (3, 4).

3. A suture clamp according to claim 2, wherein the clamp jaws (3, 4) are each formed as an arm of double-armed clamp levers (5, 6), which are positioned at the inner tube end (2) pivotably about an axis (10), and wherein the operating arms (39, 40) of the clamp levers (5, 6) are connected by way of articulated lever bars (36, 37) for articulation with the inner end (35) of the push bar (34).

4. A suture clamp according to claim 3, wherein a forked bearing head (9) with fork legs (7, 8) is provided at the inner tube end (2), the clamp levers (5, 6) being positioned pivotably about a common axis (10) between the fork legs (7, 8).

5. A suture clamp according to claim 4, wherein at least with the clamp jaws (3, 4) closed, the inner end (35) of the push bar (34) and the articulated lever bars (36, 37) are arranged between the fork legs (7, 8) of the forked bearing head (9).

6. A suture clamp according to claim 1, wherein the clamp jaws (3, 4) in their longitudinal direction (L) extend at a small acute angle (W) to the longitudinal axis (A) of the leading-in tube (1).

7. A suture clamp according to claim 1, wherein a substantially cylindrical handle member (16) is arranged at the outer tube end (15).

8. A suture clamp according to claim 7, wherein a spindle wheel (22) is pivotably supported on the handle member (16) and is longitudinally axially arrested by means of projections (26) on the spindle wheel (22) engaging with an annular circumferential groove (24) on the handle member (16).

9. A suture clamp according to claim 2, wherein for arrest of rotation, the push bar (34) is provided with a radially projecting elevation (43), which engages with an oblong hole (44) extending parallel to the longitudinal axis (A) of the leading-in tube (1).

10. A surgical suture clamp, in particular a purse string suture clamp for applying a purse string suture during the performance of gastric, intestinal and pulmonary operations, comprising two clamp jaws (3, 4) movably positioned one in relation to the other in a forceps-like manner, wherein the suture clamp is structured as an endoscopable suture clamp, to be lead into the body via a trocar, with a leading-in tube (1), in the vicinity of an inner tube end (2) of which, to be lead into the body, at least one clamp jaw (3) is positioned to be pivotably driven in relation to the second clamp jaw (4), wherein a spindle wheel (22) is pivotably supported on a handle member (16), said handle member being arranged at the outer tube end (15), and said spindle wheel being longitudinally axially arrested by means of projections (26) on the spindle wheel (22) engaging with an annular circumferential groove (24) on the handle member (16), said spindle wheel being coupled by way of a transmission (31, 34) to at least one pivotably driven clamp jaw (3, 4) for the opening and closing of the suture clamp, wherein in a closed position the clamp jaws (3, 4) in their longitudinal direction (L) extend at a small acute angle (W) to the longitudinal axis (A) of the leading-in tube (1), and wherein the clamp jaws (3,4) each comprise a needle passage (14) extending in the longitudinal direction (L) of the clamp jaws (3,4).

11. A surgical suture clamp, in particular a purse string suture clamp for applying a purse string suture during the performance of gastric, intestinal and pulmonary operations, comprising two clamp jaws (3, 4) movably positioned one in relation to the other in a forceps-like manner, wherein the suture clamp is structured as an endoscopable suture clamp, to be lead into the body via a trocar, with a leading-in tube (1), in the vicinity of an inner tube end (2) of which, to be lead into the body, at least one clamp jaw (3) is positioned to be pivotably driven in relation to the second clamp jaw (4), wherein a spindle drive with a spindle wheel (22) arrested longitudinally axially in relation to a robe axis (A) and positioned coaxially rotatably thereto and a push bar (34) arrested in the direction of rotation and longitudinally axially displaceable in the leading-in tube (1), said push bar having a radially projecting elevation (43), which engages with an oblong hole (44) extending parallel to the longitudinal axis (A) of the leading-in tube (1) which push bar (34), with an external thread (32) at its outer end, is in engagement with an internal thread (30) of the spindle wheel (22) and which, with its inner end (35), is coupled for articulation with the at least one pivotably positioned clamp jaw (3, 4) for the opening and the closing of the suture clamp, wherein in a closed position the clamp jaws (3, 4) in their longitudinal direction (L) extend at a small acute angle (W) to the longitudinal axis (A) of the leading-in tube (1), and wherein the clamp jaws (3,4) each comprise a needle passage (14) extending in the longitudinal direction (L) of the clamp jaws (3,4).

* * * * *

UNITED STATES PATENT AND TRADEMARK OFFICE
CERTIFICATE OF CORRECTION

PATENT NO. : 5,474,570
DATED : December 12, 1995
INVENTOR(S) : Kockerling, et al It is certified that error appears in the above-indentified patent and that said Letters Patent is hereby corrected as shown below:

Column 6, line 6 delete "robe" and insert --tube--.

Signed and Sealed this

Twenty-eighth Day of May, 1996

Attest:

BRUCE LEHMAN

*Attesting Officer*     *Commissioner of Patents and Trademarks*